United States Patent
Jiang et al.

(10) Patent No.: US 12,351,801 B2
(45) Date of Patent: Jul. 8, 2025

(54) USE OF GANODERMA FUNGAL RNA MOLECULES, DRUG, DRUG COMPOSITION AND DELIVERY CARRIER

(71) Applicant: MACAU UNIVERSITY OF SCIENCE AND TECHNOLOGY, Macao (CN)

(72) Inventors: Zhihong Jiang, Macao (CN); Yuan Ma, Macao (CN); Fei Ren, Macao (CN)

(73) Assignee: MACAU UNIVERSITY OF SCIENCE AND TECHNOLOGY, Macao (CN)

( * ) Notice: Subject to any disclaimer, the term of this patent is extended or adjusted under 35 U.S.C. 154(b) by 0 days.

(21) Appl. No.: 18/260,789

(22) PCT Filed: Nov. 17, 2022

(86) PCT No.: PCT/CN2022/132466
§ 371 (c)(1),
(2) Date: Jul. 10, 2023

(87) PCT Pub. No.: WO2023/165167
PCT Pub. Date: Sep. 7, 2023

(65) Prior Publication Data
US 2025/0019696 A1    Jan. 16, 2025

(30) Foreign Application Priority Data
Mar. 3, 2022   (CN) .......................... 202210203799.9

(51) Int. Cl.
C12N 15/113   (2010.01)
A61K 36/074   (2006.01)
A61P 11/06    (2006.01)

(52) U.S. Cl.
CPC .......... *C12N 15/113* (2013.01); *A61K 36/074* (2013.01); *A61P 11/06* (2018.01)

(58) Field of Classification Search
CPC ...... C12N 15/113; A61K 36/074; A61P 11/06
USPC ................... 435/6.1, 91.1, 91.31, 455, 458; 514/44 A; 536/23.1, 24.5
See application file for complete search history.

(56) References Cited

U.S. PATENT DOCUMENTS

2009/0042776 A1   2/2009  Ko et al.
2011/0189220 A1   8/2011  Yang et al.

FOREIGN PATENT DOCUMENTS

CN    114504591      5/2022
WO    2014144844     9/2014

OTHER PUBLICATIONS

Thejaswini Venkatesh et al., "tRFs: miRNAs in disguise", Gene, vol. 579, Issue 2, Dec. 29, 2015, pp. 133-138.
Ni-Ting Chiou et al., "Selective Export into Extracellular Vesicles and Function of tRNA Fragments during T Cell Activation", Cell Rep., vol. 15, No. 12, Dec. 12, 2018, pp. 1-35.
"International Search Report (Form PCT/ISA/210) of PCT/CN2022/132466," mailed on Mar. 2, 2023, pp. 1-5.
"Written Opinion of the International Searching Authority (Form PCT/ISA/237) of PCT/CN2022/132466," mailed on Feb. 14, 2023, pp. 1-5.
Yingjie Zhu et al., "Abundant and Selective RNA-Editing Events in the Medicinal Mushroom *Ganoderma lucidum*", Genetics, vol. 196, Feb. 4, 2014, pp. 1-19.
Huazhen Liu et al., "A recombinant protein rLZ-8, originally extracted from Ganoderma lucidum, ameliorates OVA-induced lung inflammation by regulating Th17/Treg balance", Journal of Leukocyte Biology, vol. 108, Jun. 24, 2020, pp. 531-545.
Ugur Sahin et al., "mRNA-based therapeutics—developing a new class of drugs", Nature Reviews Drug Discovery, vol. 13, Oct. 2014, pp. 759-780.

*Primary Examiner* — Jane J Zara
(74) *Attorney, Agent, or Firm* — JCIPRNET (57) ABSTRACT

A use of *Ganoderma* fungal RNA molecules, a drug, a drug composition and a delivery carrier are provided. It has been proved that the tRFs derived from the *Ganoderma* traditional Chinese medicine has an obvious inhibiting effect on airway smooth muscle cell phenotype change (proliferation, abnormal secretion and the like) induced by TGF-β1 and AHR, inflammation and remodeling of asthma mice induced by *Dermatophagoides pteronyssinus* in the experiments of the present disclosure, which suggests that the tRFs derived from the *Ganoderma* traditional Chinese medicine and a pharmaceutical composition can be a brand new medicine for treating asthma. The drug comprises the RNA molecule and a pharmaceutically acceptable carrier, diluent and/or excipient. The present disclosure is helpful for the research and development of asthma treatment drugs and provides reference for the research and development of other respiratory system disease treatment drugs.

7 Claims, 7 Drawing Sheets
Specification includes a Sequence Listing.

USE OF GANODERMA FUNGAL RNA MOLECULES, DRUG, DRUG COMPOSITION AND DELIVERY CARRIER

CROSS-REFERENCE TO RELATED APPLICATION

This application is a 371 of international application of PCT application serial no. PCT/CN2022/132466, filed on Nov. 17, 2022, which claims the priority benefit of China application no. 202210203799.9, filed on Mar. 3, 2022. The entirety of each of the above mentioned patent applications is hereby incorporated by reference herein and made a part of this specification.

The instant application contains a Sequencing Listing which has been submitted electronically in XML file and is hereby incorporated by reference in its entirety. Said XML copy, created on Sep. 2, 2024, is named 135915-US-sequence listing and is 11,689 bytes in size.

TECHNICAL FIELD

The present disclosure relates to a field of asthma treatment, and specifically relates to a pharmaceutical use of *Ganoderma* tRFs in asthma treatment.

DESCRIPTION OF RELATED ART

Bronchial asthma, commonly known as asthma, is a prevalent and debilitating disease that poses a significant threat to human health. According to research conducted by Academician Wang Chen, China is facing an alarming burden of asthma cases. The prevalence rate of asthma among individuals over the age of 20 in China is 4.2%, accounting for approximately 45.79 million people. Shocking, 71.2% of asthma patients have not received a clear diagnosis, and over 95% are not receiving proper standardized treatment.

Airway remodeling is a critical characteristic of asthma that occurs early stages in the pathogenesis process. It leads to irreversible airflow limitation and contributes to the poor response of patients to drug treatments. The imbalance in the phenotype of airway smooth muscle cell (ASMC) plays a significant role in asthmatic airway remodeling. In a healthy population, ASMC exhibit a "constrictive" phenotype, efficiently contracting and relaxing to maintain normal airway resistance. However, various factors such as infection, allergen and environmental triggers can induce the transformation of ASMC from the normal "constrictive" phenotype to an abnormal "proliferative/synthetic" phenotype. This transformation is characterized by excessive proliferation, hypertrophy, abnormal contraction, and secretion of ASMC. Consequently, persistent airway hyperreactivity (AHR), irreversible airflow limitation, intensified airway inflammation, and a detrimental "vicious circle" is established. Targeting the proliferation/synthesis phenotype ASMC holds promise for reversing airway remodeling, providing a novel approach to improving the overall clinical efficacy of asthma treatment and achieving long-term cure.

In recent studies, non-coding RNAs, particularly microRNAs, have demonstrated diverse regulatory effects by targeting various aspects of RNA transcription or post-transcriptional processes across eukaryotes. Lin Zhang et al (Cell research 2012, 22, 107-126) proposed that exogenous plant microRNAs present in food can be absorbed by the mammalian digestive system and subsequently transported to different organs via the bloodstream. This phenomenon enables the regulation of mammalian gene expression. *Ganoderma* (*Ganoderma lucidum*) a member of the Polyporaceae family, is a type of fungus known for its beneficial properties in invigorating lung function, warming lungs, eliminating phlegm, and relieving cough and asthma symptoms. Although *Ganoderma* itself is relatively non-toxic, the administration of *Ganoderma* injection may occasionally result in anaphylactic reaction. Extracts from *Ganoderma*, such as ganoderan, triterpene and steroid, have been extensively studied for their potential antibacterial, anti-inflammatory, anticancer, anti-aging, and immunoregulatory properties. However their clinical applications remain limited. Therefore, there is a pressing need to develop a range of drugs and treatments that are devoid of harmful side effects on human health.

SUMMARY

The technical problems to be solved are as follows. The present disclosure provides a pharmaceutical use of *Ganoderma* tRFs in asthma treatment, and the applicant screens the *Ganoderma* tRFs through a prophase ASMC cell viability experiment, obtains the *Ganoderma* tRF_31 with the best activity, and respectively verifies the *Ganoderma* tRFs in an asthma mouse model and an ASMC cell model induced by transforming growth factor (TGF)-β1. The results show that *Ganoderma* tRF_31 can inhibit the airway remodeling in asthmatic mice and reverse TGF-β1-induced "proliferative/synthetic" ASMC, which may provide a theoretical basis for the use of *Ganoderma* tRF_31 for the treatment of asthma.

The technical solutions are as follows. Provided is a use of *Ganoderma* fungal RNA molecules in preparation of asthma prevention or treatment drugs.

The RNA molecules are derived from or originate from *Ganoderma lucidum* (Curtis: Fr.) P. Karst.

The RNA molecules originate from transfer RNA molecules fragments of *Ganoderma* traditional Chinese medicine (tRNA fragment, tRFs).

A sequence of the *Ganoderma* tRFs comprises a sequence selected from SEQ ID NO. 1 to 6, a functional variant of the sequence, or a homologue of the sequence.

The tRFs molecules are double stranded RNA molecules, the tRFs molecules comprise an antisense sequence selected from SEQ ID NO. 1 to NO. 6, or a functional variant of the antisense sequence or a homologue of the antisense sequence, and a complementary sense sequence selected from SEQ ID NO. 7 to NO. 12.

The double stranded RNA molecules, or a functional variant of the double stranded RNA molecules or a homologue thereof of the double stranded RNA molecules further comprise a 3' suspension.

The double stranded RNA molecules, or the functional variant of the double stranded RNA molecules, or the homologue of the double stranded RNA molecules, wherein a nucleotide sequence of an antisense and/or sense strand of the double stranded RNA molecules, the functional variant of the double stranded RNA molecules, or the homologue of the double stranded RNA molecules, comprises at least one chemically modified nucleotide; the chemical modification is selected from at least one of 1-methyl, 2-methyl, 5-methyl, 7-methyl, N2-methyl, N6-methyl, N2,N2-dimethyl, 2'-O-methyl, N6-isopentenyl, 2-methylthio-N6-isopentenyl, N6-threonic carbamoyl, N6-methyl-N6-threonic carbamoyl, 2-thio, 4-thio, N4-acetyl, 5-formyl, 3-(3-amino-3-carboxypropyl), 5-methoxy, 5-oxyacetic acid, 5-oxyacetic acid methyl ester, 5-methoxycarbonylmethyl, 5-methoxycarbonylmethyl-2'-O-methyl, 5-methoxycarbonylmethyl-2- thio, 5-aminomethyl-2-thio, 5-methylaminomethyl, 5-methylaminomethyl-2-thio, 5-aminoformylmethyl, 5-aminoformylmethyl-2'-O-methyl, 5-carboxymethylaminomethyl, 5-carboxymethylaminomethyl-2'-O-methyl, 5-carboxymethylaminomethyl-2-methyl, 5-taurine methyl, and 5-taurinemethyl-2-thio.

Provided is a drug for preventing or treating asthma. The active ingredient comprises at least one of the transfer RNA molecules from *Ganoderma* traditional Chinese medicine or a functional variant of the transfer RNA molecules or a homologue of the transfer RNA molecules, and an optionally pharmaceutically acceptable carrier, diluent and/or excipient.

The drug composition further comprises a nucleic acid stabilizer.

A delivery carrier for preventing and treating asthma. The delivery carrier comprise the double stranded RNA molecules or the functional variant of the double stranded RNA molecules or the homologue of the double stranded RNA molecules, and an optionally a pharmaceutically acceptable carrier, diluent and/or excipient.

Specifically, (1) a TGF-β1-induced ASMC cell model is established, in which the cell vitality and the anti-proliferation effect of the lucid *Ganoderma* tRFs are detected, *Ganoderma* tRF_31 is selected for intervention, and the effect of balancing the ASMC phenotype of the lucid *Ganoderma* tRF_31 is further determined from the cell level through the testing of indexes such as inflammation, fibrosis and proliferation. (2) A house dust mite induced mouse asthma animal model is established, in which an asthma mouse model is constructed by a *Dermatophagoides pteronyssinus* nose dropping method, and the inhibition effect of *Ganoderma* tRF-31 nose dropping drug on asthma airway remodeling is determined.

The experimental method mainly includes the following parts.

1. Establishment of TGF-β1-Induced ASMC Cell Model and Activity Screening of *Ganoderma* tRFs.

Primary human ASMC is cultured in vitro. The influence of TGF-β1 with different concentrations on the proliferation of human ASMC is detected by adopting a cell counting kit-8 (CCK-8) method; the influence of the *Ganoderma* tRFs with different concentrations on the activity of human ASMC and the influence of TGF-β1 induced human ASMC proliferation are detected by the CCK-8 method; the effect of *Ganoderma* tRF-31 on TGF-β1-induced human ASMC "proliferation/synthesis type" is detected by 5-ethynyl-2'-deoxyuridine (EdU), enzyme-linked immunosorbent assay (ELISA), western blot.

2. Construction of Asthma Mouse Model and Pharmacodynamic Study of *Ganoderma* tRF-31.

Firstly, an asthma mouse model is constructed by using *Dermatophagoides pteronyssinus* nasal drops, lung function of a mouse is detected, Immunoglobulin E (IgE) in bronchoalveolar lavage fluid (BALF) is detected and a pathological section is carried out, which display that the modelling is successful. The changes of lung function, inflammatory factor level in BALF, degree of lung tissue fibrosis and the like of mice in house dust mite molding and *Ganoderma* tRF-31 treatment groups are compared.

3. Statistical Analysis Method

Quantitative results are depicted as means±standard error (+SEM) and data statistics are performed using One-Way ANOVA test and Dunnett post hoc test by Prism 6.00 and SPSS 20 statistical software. Significant statistical significance is judged by $P<0.05$.

Through observations of inflammatory factor level, cell proliferation and cell morphology, it is found that the *Ganoderma* tRFs can balance the ASMC phenotype at the cell level, and the effect of *Ganoderma* tRF_31 is particularly significant. According to the pathological observation and testing of inflammation and fibrosis indexes, it is found in the present disclosure that the *Ganoderma* tRF_31 can obviously inhibit airway remodeling of asthmatic mice at the whole animal level. The above results suggest that the *Ganoderma* tRFs can be a novel drug for treating asthma. Specifically, the *Ganoderma* tRFs can be synthesized, modified appropriately, and encapsulated by appropriate carriers such as nanoparticles, liposomes to form a drug, and asthma can be treated by nasal drops, oral administration and the like.

The beneficial effects lie in the following. As a new tool for regulating and controlling gene expression, the *Ganoderma* tRFs is a novel targeted molecular therapeutic drug, which is different from the traditional therapeutic drug, has the advantages of easy synthesis, easy testing, accurate quantification, capability of enhancing the stability and improving the affinity after chemical modification, capability of effectively positioning to target organs through a special drug delivery system and the like. And it can greatly improve the specificity and the targeting property of asthma treatment. The successful development of this *Ganoderma* tRFs drug will create a new situation for the treatment of asthma and provide reference for the development of other disease treatment drugs. The present disclosure researches the influence and inhibition effect of the *Ganoderma* tRFs on the airway remodeling of asthma at the cellular level and the whole animal level, and discloses the potential value of the *Ganoderma* tRFs as a therapeutic drug. Therefore, the present disclosure can provide a help for developing a novel small molecule drug target with a potential therapeutic value.

BRIEF DESCRIPTION OF THE DRAWINGS

FIG. 2 illustrates CCK-8 method for detecting that *Ganoderma* tRFs inhibits ASMC proliferation induced by TGF-β1. A is the effect of TGF-β1 on ASMC proliferation; B is the effect of LZ_2 on ASMC proliferation induced by TGF-β1; C is the effect of LZ_9 on ASMC proliferation induced by TGF-β1; D is the effect of LZ_10 on ASMC proliferation induced by TGF-β1; E is the effect of LZ_11 on ASMC proliferation induced by TGF-β1; F is the effect of LZ_25 on ASMC proliferation induced TGF-β1; G is the effect of LZ_31 on ASMC proliferation induced by TGF-β1. In #$P<0.05$, there is a statistical significance to compare difference with the control group; in *$p<0.05$, there is a statistical significance to compare difference with the TGF-β1 group. TGF-β1 (5 ng/ml) and *Ganoderma* tRNAs (25 nM) are selected for the subsequent experiments.

A and B of FIG. 3 illustrate EdU method for detecting that *Ganoderma* tRFs inhibits ASMC proliferation induced by TGF-β1. In #P<0.05, there is a statistical significance to compare difference with the control group; in *p<0.05, there is a statistical significance to compare difference with the TGF-β1 group.

A and B of FIG. 8. illustrate a change and a semi-quantitative analysis in lung tissue fibrosis after the construction of the house dust mite-sensitized asthma mouse model. In #P<0.05, there is a statistical significance to compare difference with the control group; in *p<0.05, there is a statistical significance to compare difference with the HDM group.

DESCRIPTION OF THE EMBODIMENTS

Unless defined otherwise, all technical terms used in the present disclosure have the same meaning as commonly understood by the persons skilled in the art. As used herein, "comprising" means including the following elements but not excluding others. "consisting of" means being formed from the corresponding elements.

The RNA molecules adopted according to the present disclosure can be naturally occurring, modified or artificially synthesized according to the sequences disclosed in the present disclosure, and preferably the RNA molecules are derived from or originate from a fungus of the *Ganoderma lucidum*. The RNA molecules of the present disclosure are not provided in the form of boiled extracts obtained from fungi, such as decoctions, because it can be understood that RNA molecules are susceptible to spontaneous degradation at high temperatures, alkaline pH and in the presence of nucleases or divalent metal ions.

The RNA molecules of the present disclosure have a sequence length of approximately 10 to 200 nucleotides, which can be considered as small RNA molecules. Preferably, the sequence length of the RNA molecule is from approximately 10 to approximately 50 nucleotides.

The RNA molecule of the present disclosure or a functional variant or homologue thereof is selected from the sequences of SEQ ID NO. 1 to NO. 6. The term "functional variant" of an RNA molecule refers to a molecule that is substantially similar to the RNA molecule, having one or more sequence alterations that do not affect the biological activity or function of the RNA molecule. Sequence alterations that do not affect the functional properties of the resulting RNA molecule are well known in the art. For example, nucleotide changes that result in changes in the-5'-end and the-3'-end portions of the molecule are not expected to alter the activity of the polynucleotide.

In particular, a functional variant of an RNA molecule has an overall sequence identity of at least 80%, 81%, 82%, 83%, 84%, 85%, 86%, 87%, 88%, 89%, 90%, 91%, 92%, 93%, 94%, 95%, 96%, 97%, 98% or 99% to a non-variant RNA molecule according to the present disclosure.

The term "homologue" in the present disclosure refers to a nucleotide having a sequence identity of at least 50%, at least 60%, at least 70%, at least 80%, at least 90% or at least 95% to an RNA molecule according to the present disclosure. In one embodiment, a homologue of an RNA molecule has an overall sequence identity of at least 90%, 91%, 92%, 93%, 94%, 95%, 96%, 97%, 98% or 99% to the RNA molecule.

The RNA molecules of the present disclosure can be administered in the form of a pharmaceutical composition comprising the RNA molecule and at least one pharmaceutically acceptable excipient. The pharmaceutically acceptable excipient can be one or more of diluents, fillers, binders, disintegrants, lubricants, colorants, surfactants, gene delivery vehicles, and preservatives. The pharmaceutical composition can be present in solid, semi-solid or liquid form, preferably in a liquid form. The pharmaceutical preparation can be liposome lyophilized powder; polypeptide nano freeze-dried powder; a spray; tablets and the like. The pharmaceutical composition may comprise further pharmaceutical active ingredients. The skilled person is able to select a suitable pharmaceutically acceptable excipient according to the form of the pharmaceutical composition and is aware of the method of preparing the pharmaceutical composition and is able to select a suitable method of preparing the pharmaceutical composition according to the kind of pharmaceutically acceptable excipient and the form of the pharmaceutical composition.

The present disclosure is described in detail below with reference to the following drawings and examples. This example is implemented on the premise of the technical solutions of the present disclosure, and gives a detailed embodiment and a process, but the scope of the present disclosure is not limited to the following examples. Conditions, methods and the like not described in the following examples are carried out conventionally.

The reagents used in the following examples are analytical grade reagents and can be commercially available from a regular source.

The antisense sequences of SEQ ID NO. 1 to NO. 6 and the sense sequences of SEQ ID NO. 7 to NO. 12 as shown in Table 1 can be artificially synthesized according to the

TABLE 1

List of RNA Molecules Derived from tRNA Sequence from *Ganoderma Lucidum* (Curtis: Fr.) P. Karst. by Artificial Synthesis

| SEQ ID NO. | Antisense sequence (5' to 3') | SEQ ID NO. | Sense sequence (5' to 3') | Length (protomer) |
| --- | --- | --- | --- | --- |
| 1 | GGGGAUAUCUGAUAAUUGG | 7 | CCAAUUAUCAGAUAUCCCC | 19 |
| 2 | GGGCCCUUAGCUUAAUAGGUAG | 8 | CUACCUAUUAAGCUAAGGGCCC | 22 |
| 3 | GGGCCCUUAGCUUAAUAGG | 9 | CCUAUUAAGCUAAGGGCCC | 19 |
| 4 | UGAGUUGUAGUUUAAUUGGGA | 10 | UCCCAAAUUAAACUACAACUCA | 22 |
| 5 | GCCAAAAUAGUUUAAAUGGUUA | 11 | UAACCAUUUAAACUAUUUUGGC | 22 |
| 6 | UCGAGUCUAUCUAUCUCCACCA | 12 | UGGUGGAGAUAGAUAGACUCGA | 22 |

TABLE 2

List of Abbreviations of Modification Symbols in tRNA sequences

| Modification symbols | Common name |
| --- | --- |
| m1A | 1-methyladenosine |
| m2A | 2-methyladenosine |
| m6A | N6-methyladenosine |
| Am | 2'-O-methyladenosine |
| i6A | N6-isopentenyl adenosine |
| ms2i6A | 2-methylmercapto-N6-isopentenyl adenosine |
| t6A | N6-threadyl aminoacyl adenosine |
| m6t6A | N6-methyl-N6-threadyl aminoacyl adenosine |
| I | Inosine |
| m5C | 5-methylcytidine |
| Cm | 2'-O-methylcytidine |
| s2C | 2-thiocytidine |
| ac4C | N4-acetylcytidine |
| f5C | 5-formylcytidine |
| k2C | Lysidine |
| m1G | 1-methylguanosine |
| m2G | N2-methylguanosine |
| m7G | 7-methylguanosine |
| Gm | 2'-O-methylguanosine |
| m22G | N2,N2-dimethylguanosine |
| Q | Queuosine |
| galQ | Galactosyl-queuosine |
| ψ | Pseudouridine |
| D | Dihydrouridine |
| T | 5-Methyluridine |
| Um | 2'-O-Methyluridine |
| s2U | 2-thiouridine |
| s4U | 4-thiouridine |
| acp3U | 3-(3-Amino-3-carboxypropyl) uridine |
| mo5U | 5-methoxyuridine |
| cmo5U | Uridine 5-Oxyacetic Acid |
| mcmo5U | Uridine 5-Oxyacetic Acid Methyl Ester |
| mcm5U | 5-Methoxycarbonylmethyluridine |
| mcm5Um | 5-Methoxycarbonylmethyl-2'-O-methyluridine |
| mcm5s2U | 5-Methoxycarbonylmethyl-2-thiouridine |
| nm5s2U | 5-Aminomethyl-2-thiouridine |
| mnm5U | 5-Methylaminomethyluridine |
| mnm5s2U | 5-Methylaminomethyl-2-thiouridine |
| ncm5U | 5-Aminoformylmethyluridine |
| ncm5Um | 5-Aminoformylmethyl-2'-O-methyluridine |
| cmnm5U | 5-Carboxymethylaminomethyluridine |
| cmnm5Um | 5-Carboxymethylaminomethyl-2'-O-methyluridine |
| cmnm5s2U | 5-Carboxymethylaminomethyl-2-methyluridine |
| tm5U | 5-Taurine Methyluridine |
| tm5s2U | 5-Taurine methyl-2-thiouridine | present disclosure. The derived sequence fragments are divided into the following two categories: the first is 5'-tRNAs which includes fragments with a length of 2 to 35 nucleotides formed by cutting off the 5' end of the mature tRNA sequence at the D ring, D ring arm, anti codon ring, or anti codon ring arm; The second type is 3'-tRFs which includes fragments with a length of 2 to 35 nucleotides formed by cutting off the 3'-CCA end of the mature tRNA sequence at the T ring, T ring arm, anti codon ring, or anti codon ring arm. Each sense sequence and the corresponding antisense sequence forms a double stranded RNA molecule.

Furthermore, the RNA molecule of the present disclosure may include a 3' suspension, preferably a 3' suspension comprising 2 nucleotides. A provided 3' suspension improves the stability of the RNA molecule.

Example 1: Establishment of TGF-β1-Induced ASMC Cell Model and Activity Screening of *Ganoderma* tRFs (1) Culture of Primary Human Airway Smooth Muscle Cells
1) Preparation of Culture Medium
Complete culture medium: the prepared complete culture medium is stored in a dark place at 4° C. in the presence of 2 mL of FBS, 1 mL of smooth muscle cell growth factor, and 1 mL of penicillin/streptomycin solution (100×) per 100 mL of SMCM.
2) Cell Recovery
The ASMC frozen pipe is removed from the liquid nitrogen and immediately placed in a preheated 37° C. water bath and shaken rapidly until completely thawed.
Thawed frozen cells are transferred to a culture bottle, an appropriate amount of preheated 37° C. complete culture medium is added, and cultured in a CO2 incubator (5% CO2, 37° C.). After the cells have fully adhered to the wall, the medium is changed, and then the medium is changed every 2 days.
The normal grown ASMC is in a long spindle shape and can be mutually overlapped, and the ASMC can be in a valley-peak shape when the growth reaches more than 90%.
3) Cell Passage
When the cells grow to approximately 80% of the culture flask, the cells are digested with 0.25 wt. % pancreatin (containing 0.02 wt. % EDTA). Under a phase contrast microscope, a cell shrinkage and clear cell gaps can be seen, a complete culture medium is added to stop digestion, centrifuged at 1000 rpm for 5 minutes. The liquid is discarded, a new complete culture medium is added, uniformly mixed before the cell passage. Before intervention, cells are starved for 6 hours to 8 hours by using SMCM without FBS.

(2) Cell Viability Testing

1) The CCK-8 Method is Used for Detecting the Cell Viability.

Figure 1:
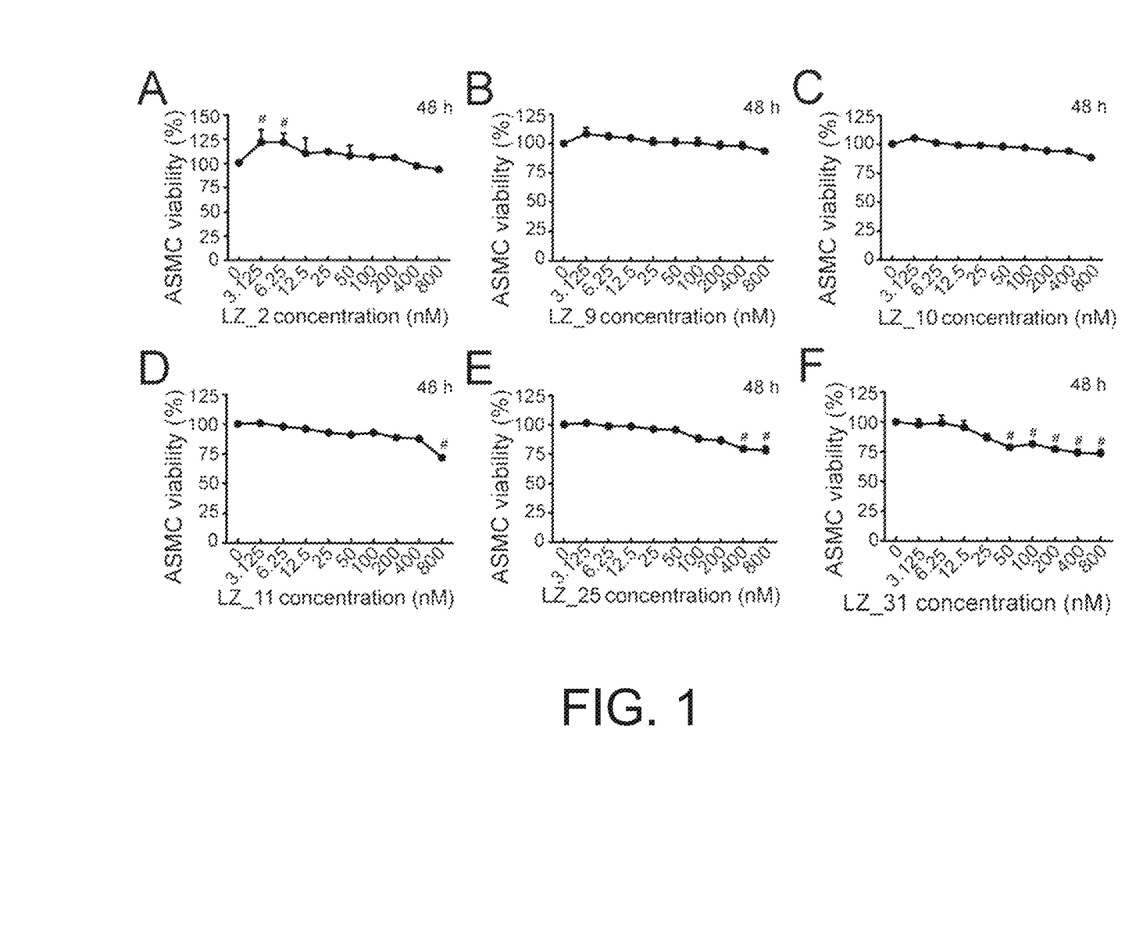
FIG. 1 illustrates the CCK-8 method for detecting an effect of *Ganoderma* tRFs on ASMC activity. A is the effect of LZ_2 on the viability of ASMC; B is the influence of LZ_9 on the ASMC activity; C is the influence of LZ_10 on the ASMC activity; D is the influence of LZ_11 on the ASMC activity; E is the effect of LZ_25 on the ASMC activity; F is the effect of LZ_31 on ASMC viability. In the figure, LZ refers to the *Ganoderma* source. LZ_2, LZ_9, LZ_10, LZ_11, LZ_25 and LZ_31 correspond to the double-stranded RNA molecules shown in SEQ ID NO. 1 to NO. 6, respectively. In #$P<0.05$, there is a statistical significance to compare difference with the control group.

As illustrated in FIG. 1, ASMC in logarithmic phase is taken and inoculated into 96-well plates for incubation, with 5000 cells per well. Multiple wells and zero-setting wells are set for each group, with only drug and no cells added to the zero-setting wells. After the cells grow and fuse to approximately 70%, the cells are starved, and then the medium is removed and the cells are treated for 24 hours and 72 hours with 100 μL/well of *Ganoderma* tRFs solutions prepared in medium with different concentration gradients (0, 3.125, 6.25, 12.5, 25, 50, 100, 200, 400, 800 nM). At the corresponding time points, 10 μL of CCK-8 reagent is added to each well (please take care to prevent air bubbles from forming so as not to affect the determination of OD values), and incubation was continued for approximately 1 hour to 2 hours. The absorbance value (OD value) is measured at a wavelength of 450 nm in a microplate reader. Percent (%) cell viability=(the average absorbance of the treated group–the absorbance value of the zero well of the treated group)/(the average absorbance of the control group–the absorbance value of the zero well of the control group)×100%.

Figure 2:
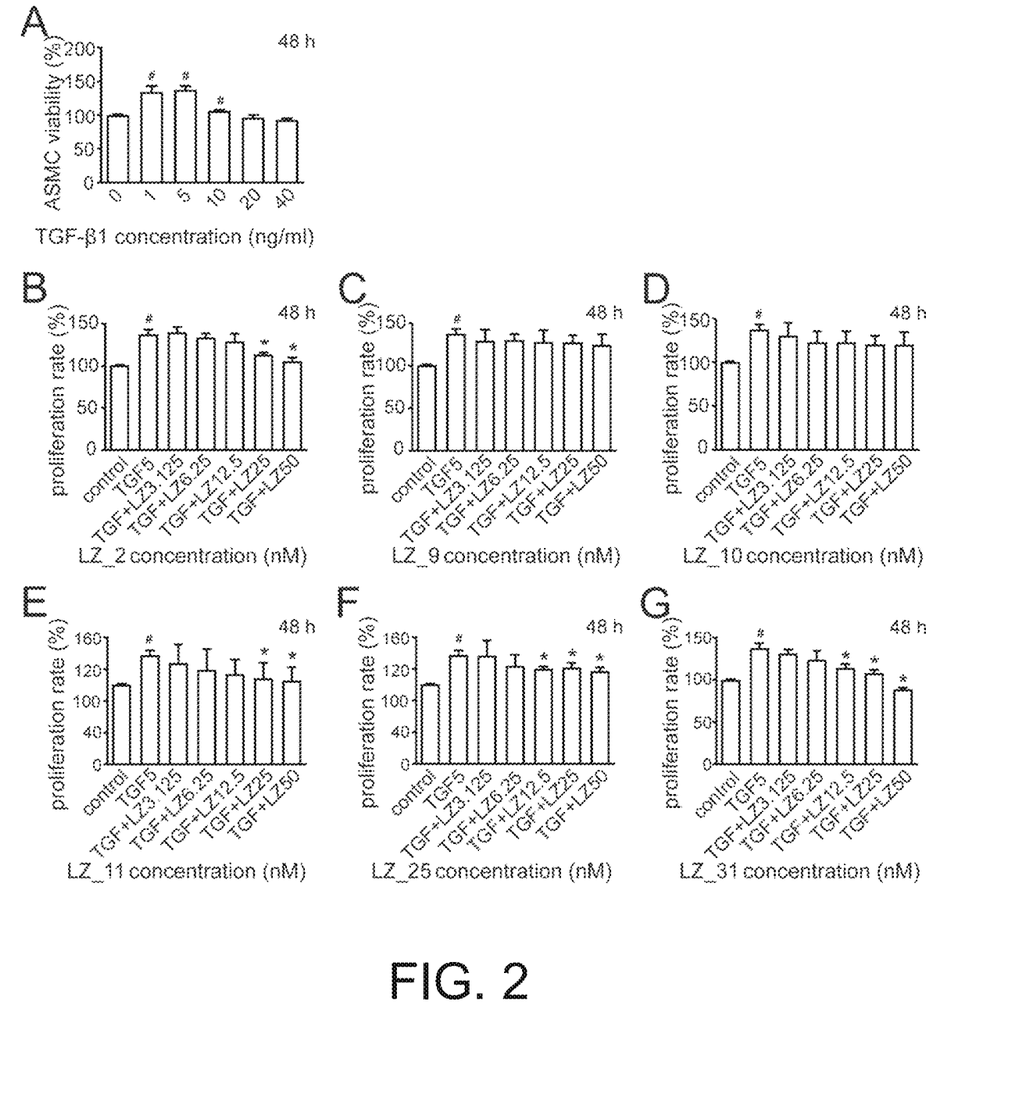

The proliferation of human ASMC is tested at different concentrations of TGF-β1 (0.1, 1, 10, 100 ng/ml) in the same manner as illustrated in A of FIG. 2. As illustrated in FIG. B-G of 2, 5 ng/ml TGF-β1 is selected as the concentration for the subsequent experiments according to the experimental results. And the CCK-8 method is used for detecting the influence of *Ganoderma* tRFs with different concentrations (3.125, 6.25, 12.5, 25 and 50 nM) on the proliferation of human ASMC induced by 5 ng/ml TGF-β1.

2) Testing on the Cell Proliferation Capacity by an EdU Method

Figure 3:
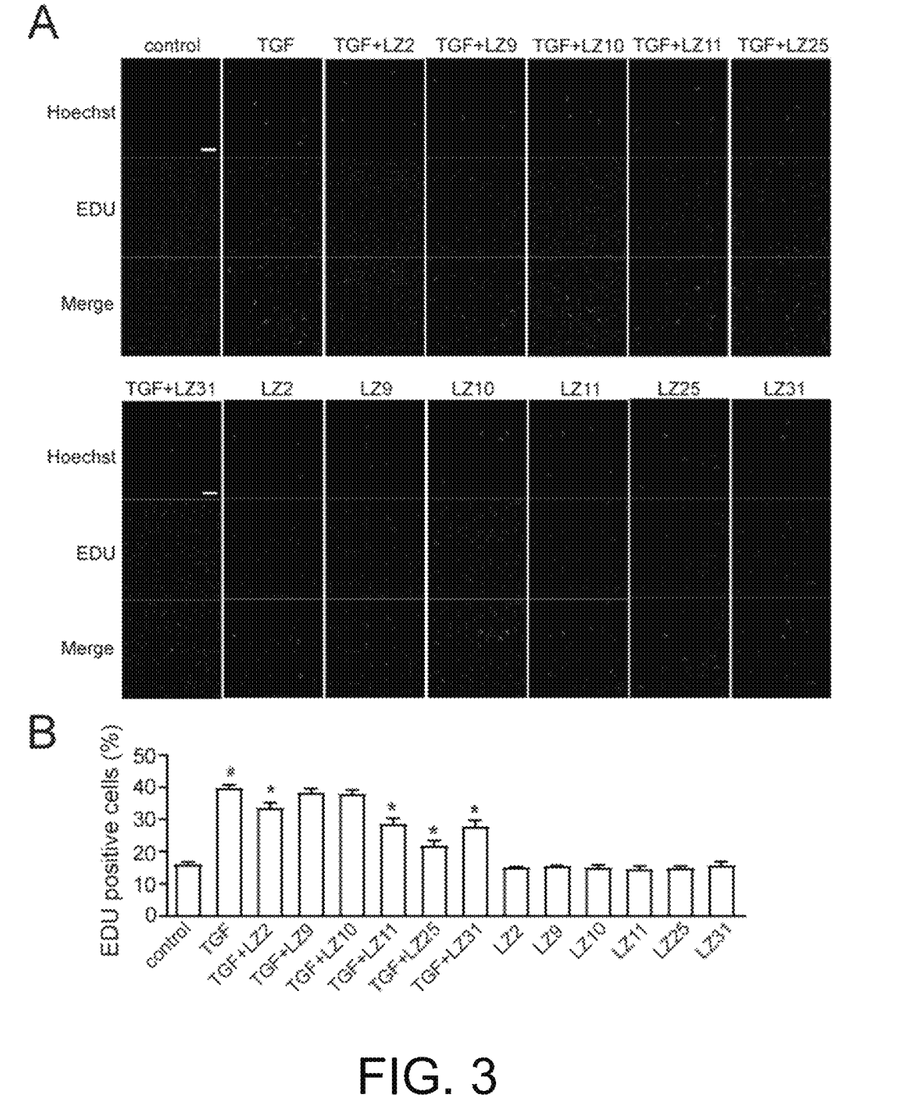

As illustrated in FIG. 3, the cell culture is performed in the same manner as in the CCK-8 method. After starvation, the cells are divided into 14 groups: control group, TGF-β1 (5 ng/mL) group, TGF-β1 (5 ng/mL)+*Ganoderma* tRF_2 (25 nM) group, TGF-β1 (5 ng/mL)+*Ganoderma* tRF_9 (25 nM) group, TGF-β1 (5 ng/mL)+*Ganoderma* tRF_10 (25 nM) group, TGF-β1 (5 ng/mL)+*Ganoderma* tRF_11 (25 nM) group, TGF-β1 (5 ng/mL)+*Ganoderma* tRF_25 (25 nM) group, TGF-β1 (5 ng/mL)+*Ganoderma* tRF_31 (25 nM) group, *Ganoderma* tRF_2 (25 nM), *Ganoderma* tRF_9 (25 nM), *Ganoderma* tRF_10 (25 nM), *Ganoderma* tRF_11 (25 nM), *Ganoderma* tRF_25 nM (25 nM) and *Ganoderma* tRF_31 (25 nM) group. After 48 hours of treatment on the cells separately, all manipulations are performed according to the EdU kit instructions.

① EdU Labelling

A cell culture medium and an EdU solution (reagent A) are diluted according to a volume ratio of 1000:1 to prepare an appropriate amount of 50 μM EdU culture medium.

Each well is added with 100 μL of 50 μM EdU culture medium, incubated for 2 hours in the incubator.

The culture medium is discarded and each well is washed 1 to 2 times with phosphate-buffered saline (PBS) for 5 minutes each time.

② Cell Immobilization

Each well is added with 50 μL of cell fixative (PBS containing 4 wt. % paraformaldehyde), incubated for 30 minutes at the room temperature, and the fixative is discarded.

Each well is added with 50 μL of 2 mg/mL glycine, incubated for 5 minutes on a shaking table, and then the glycine solution is discarded.

Each well is washed with PBS for 5 minutes (100 μL per well on shaker) and the PBS is discarded.

(Enhanced) Each well is added with 100 μL of osmotic agent (PBS containing 0.5 wt. % TritonX-100) and incubated on a destaining shaker for 10 minutes, and washed with PBS for one time for 5 minutes.

③ Apollo Staining

1× Apollo® staining reaction solution is prepared according to the instructions, each well is added with 100 μL of prepared staining solution in a dark, room temperature, incubated in a decolorization shaker for 30 minutes, and the staining reaction solution is discarded.

Each well is added with 100 μL of penetrant, washed in the decolorization shaker for 2 to 3 times, 10 minutes each time, and the penetrant is discarded.

(Enhanced) Each well is added with 100 μL of methanol for washing for 1 to 2 times, each time for 5 minutes; each well is washed with PBS for one time for 5 minutes.

④ DNA Staining

Deionized water and a reagent F is diluted according to a ratio of 100:1, to prepare an appropriate amount of 1× Hoechst33342 reaction solution, and stored in a dark place.

Each well is added with 100 μL of 1× Hoechst33342 reaction solution, incubated for 30 minutes on a decolorization shaker at the room temperature in a dark place, and the staining reaction solution is discarded.

Each well is added with 100 μL PBS for washing for 1 to 3 times.

⑤ Image Acquisition and Analysis

Each well is immediately observed with a fluorescence microscope after staining is completed; when conditions are limited, each well is sealed after preparing with glycerol and PBS 1:1 and stored in a dark place at 4° C. for testing, but should not exceed 3 days.

(3) Determination of Adhesion Molecule Levels in Cell Supernatants

Figure 4:
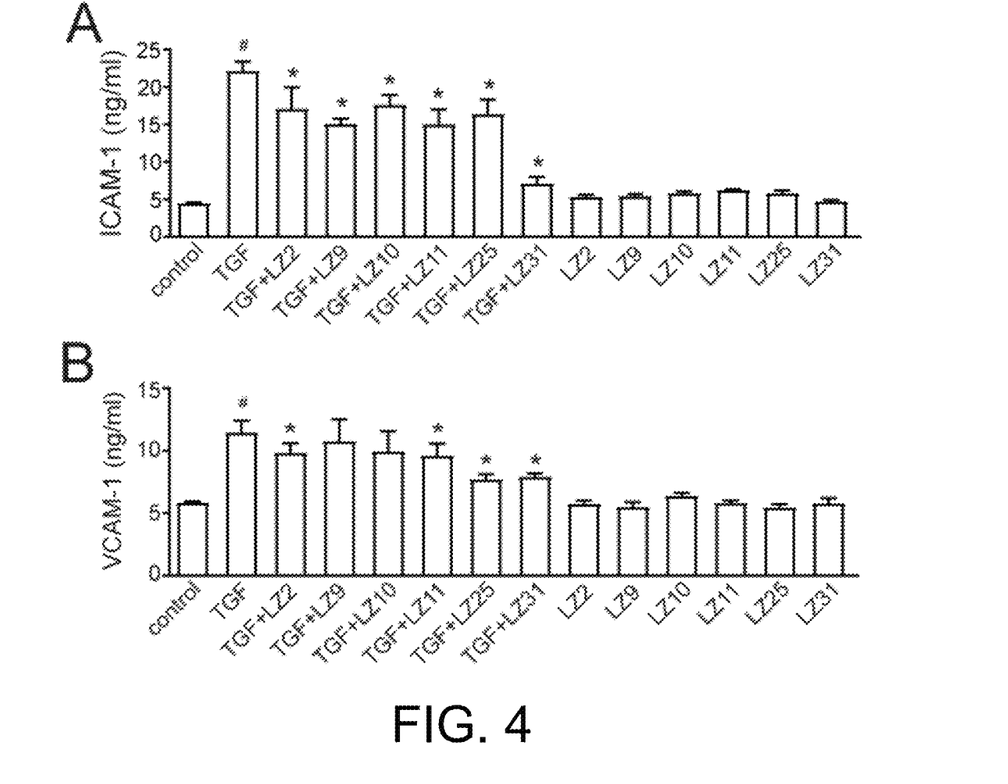
FIG. 4 illustrates ELISA verifies that *Ganoderma* tRFs inhibits the expression of ASMC adhesion molecules induced by TGF-β1. A is the influence of *Ganoderma* tRFs on the expression of ICAM-1 induced by TGF-β1; B is the influence of *Ganoderma* tRFs on the expression of VCAM-1 induced by TGF-β1. In #P<0.05, there is statistically significant to compare difference with the control group; *p<0.05, there is statistically significant to compare difference with the TGF-β1 group.

As illustrated in FIG. 4, the procedures are performed according to the human intercellular cell adhesion molecule-1 (ICAM-1) and vascular cell adhesion molecule-1 (VCAM-1) ELISA testing kit instructions, respectively.

1) Human ICAM-1 Testing

1. Required reagents, standard product diluent and control are prepared and balanced to the room temperature.

2. Each well is added with 100 μL of ICAM-1 enzyme labeling reagent.

3. 100 μL of standard substance, control and sample to be detected are added into corresponding wells, and multiple wells are set.

4. Each well is patted for 1 minute, attached with a sealing film, and incubated for 1.5 hours at the room temperature.

5. The solution is discarded, the plate is washed for 4 times, and patted to dry.

6. Each well is added with substrate developing-coloring solution (200 μL each well), kept out of the light, and incubated for 30 minutes at the room temperature.

7. Each well is added with 50 μL of reaction stop solution, and vibrated lightly and mixed uniformly.

8. Within 30 minutes after the end of the reaction, the plate is read in ELISA format (450 nm) by a microplate reader. An ICAM-1 ELISA standard curve is made, and the concentration of ICAM-1 in each sample is calculated.

2) Human VCAM-1 Testing

1. Required reagents, standard product diluent and control are prepared and balanced to the room temperature.

2. Each well is added with 100 μL of VCAM-1 enzyme labeling reagent.

3. 100 μL of standard substance, control and sample to be detected are added into corresponding wells, and multiple wells are set.

4. Each well is patted for 1 minute, attached with a sealing film, and incubated for 1.5 hours at the room temperature.

5. The solution is discarded, the plate is washed for 4 times, and patted to dry.

6. Each well is added with the substrate developing-coloring solution (200 μL each well), kept out of the light, and incubated for 30 minutes at the room temperature.

7. Each well is added with 50 μL of reaction stop solution, and lightly vibrated and uniformly mixed.

8. Within 30 minutes after the end of the reaction, the plate is read in ELISA format (450 nm) by a microplate reader. A VCAM-1 ELISA standard curve is made and the concentration of VCAM-1 in each sample is calculated.

(4) Extraction of Total Cell Protein and Western Blot Experiment

Figure 5:
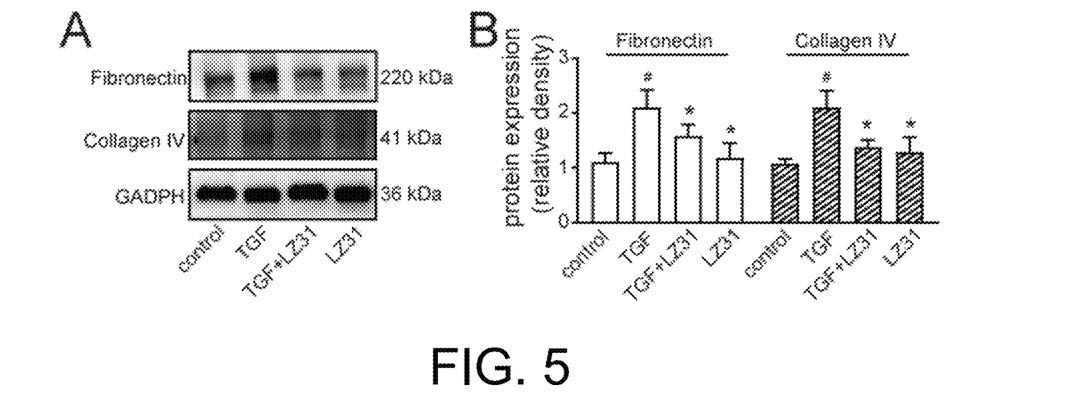
FIG. 5 illustrates Western blot verifies that *Ganoderma* tRF_31 inhibits the deposition ASMC extracellular matrix induced by TGF-β1. A is the effects of LZ_31 on the expressions of fibronectin and type IV collagen induced by TGF-β1; B is a semi-quantitative analysis of A. In #P<0.05, there is a statistical significance to compare difference with the control group; in *p<0.05, there is a statistical significance to compare difference with the TGF-β1 group.

Cell lysate is prepared (1 mL of RIPA lysate, 10 μL of PMSF is added to make the final concentration of 1 mM before use), after the culture medium in each well of the six well plate is discarded, each well is cleaned once with 1 mL of PBS, added with 80 μL of the prepared lysate, and shaken at 4° C. for 30 minutes. Centrifugation is carried out at 12,000 rpm for 15 minutes at 4° C. to collect the supernatant. Western blot experiments are used in ASMC to detect changes in levels of fibronectin (FN) and IV type collagen (Collagen IV). The result is as illustrated in FIG. 5, in comparison with the TGF-β1 group, *Ganoderma* tRF_31-transfected ASMC can inhibit FN and Collagen IV expression.

Example 2: Construction of Asthma Mouse Model and Pharmacodynamic Study of *Ganoderma* tRF-31

The modeling method of the chronic asthma model comprises the following steps. 36 SPF grade BABL/c female mice weighing 18 g to 22 g at 6 weeks to 8 weeks are selected and randomly divided into 6 groups with 6 mice in each group. Control group (control), asthma group (HDM), *Ganoderma* tRF_31 low dose (HDM+LL, *Ganoderma* tRF_31 1 nmol/time), *Ganoderma* tRF_31 high dose (HDM+LH, *Ganoderma* tRF_31 5 nmol/time), dexamethasone (HDM+DEX) and solvent control (OVA+RNase free water). A model group is as follows: 25 μg of HDM-soluble protein is added to 25 μL of PBS to prepare an HDM-sensitized solution (ready for use). In 0 to 6 weeks, mice are given HDM sensitization solution nasal drops 5 days a week. In 5 weeks to 6 weeks, 1 hour before each nasal drop of HDM for sensitization, the treated group of *Ganoderma* tRF_31 is subjected to nasal drop of *Ganoderma* tRF_31 solution, the group of HDM+DEX is subjected to intraperitoneal injection of DEX solution, the solvent control group is subjected to nasal drop of RNase free water, and the treatment method is the same as the model group. Each group of mice is tested for lung function 24 hours after the last challenge, and BALF and lung tissue are collected for subsequent experiments.

(1) Testing of Lung Function in Mice

Figure 6:
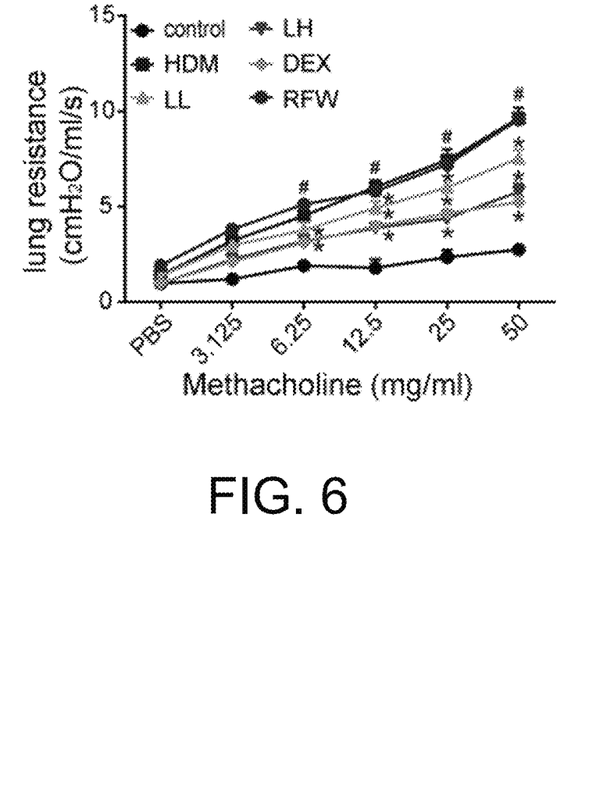
FIG. 6 illustrates lung function changes after a house dust mite-sensitized asthma mouse model is constructed. LL refers to a low dose of LZ_31 and LH refers to a high dose of LZ_31. In #P<0.05, there is a statistical significance to compare difference with the control group; in *p<0.05, there is a statistical significance to compare difference with the HDM group.

And the whole-volume tracing animal lung function instrument and the connected computer are opened, and the air tightness of the device is detected and zero calibration is performed. The mice are anesthetized with 70 mg/k pentobarbital and placed supine on the operating table, with the extremities and teeth fixed. The skin, subcutaneous tissue and muscle sections are dissected open at the neck of the mouse to fully expose the trachea. A small opening is cut by an ophthalmic scissors, a mouse trachea cannula core is placed in the small opening, and the cannula core and the trachea are fixed by a surgical suture. The mouse connected with a trachea cannula is placed on the operating platform of the lung function instrument, and the core of the trachea cannula is connected to the instrument to check whether the device is closed nor not. The lung function nebulization and test buttons are actuated to record the values for mouse airway resistance and lung compliance after inhalation of 0, 3.125, 6.25, 12.5, 25 and 50 mg/mL acetylcholine, respectively, each concentration value is traced for at least 3 minutes and recorded, each measurement interval is 5 minutes. The pressure in the container varies with the respiration of the mouse, and the respiration curve of the mouse is obtained by measuring the change of the pressure in the container, and the result is as illustrated in FIG. 6.

(2) BALF Sample Acquisition as Well as Cell Separation and Enumeration

Figure 7:
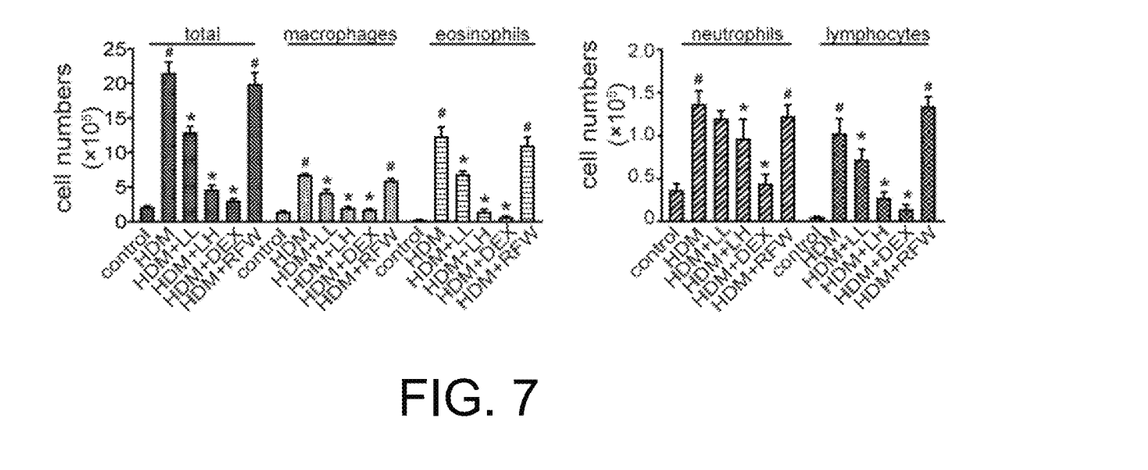
FIG. 7. illustrates the total number of cells and the classification count of cells (macrophages, eosinophils, neutrophils, lymphocytes) in BALF after a construction of the house dust mite-sensitized asthma mouse model. In #P<0.05, there is a statistical significance to compare difference with the control group; in *p<0.05, there is a statistical significance to compare difference with the HDM group.

After the lung function testing, the mice are placed on their backs on the operating table, and the limbs and teeth are fixed. PBS is slowly injected into the trachea cannula of the mouse three times, each time 0.4 mL, and slowly pumped back, approximately 1 mL in total. PBS is stored on ice and centrifuged within 2 hours. The resulting BALF is centrifuged at 4° C. for 5 minutes at 1000 rpm, and the supernatant is stored at −80° C. after being dispensed. The cell pellet is resuspended in 0.1 mL PBS, the total number of cells is determined using a hemacytometer, and the differential cell count is performed by using the Giemsa-Richardson complex staining method, and the results are as illustrated in FIG. 7.

(3) Pathological Section Staining of Mouse Lung Tissue

Figure 8:
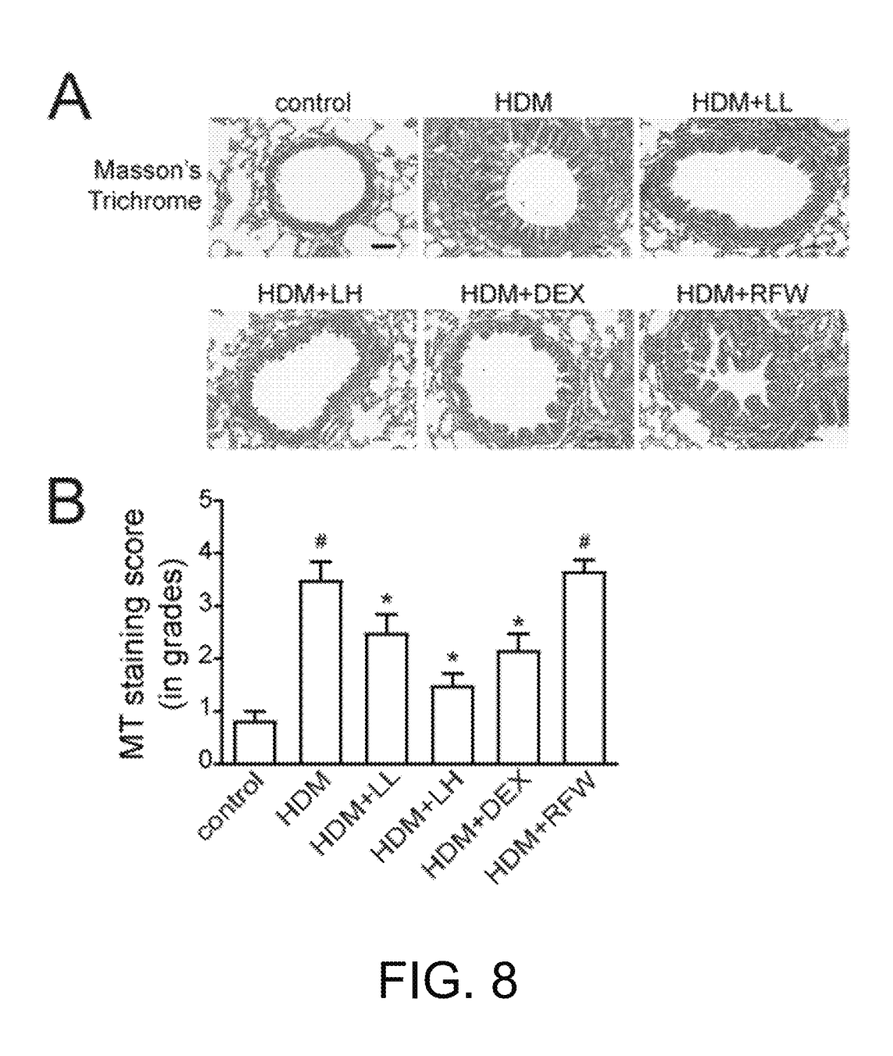

After bronchoalveolar lavage of mice, the thorax is opened, the needle connected to a 20 mL syringe is inserted into the right ventricle, and 10 mL to 15 mL of PBS is slowly injected. A trachea cannula is inserted and fixed internally with 10 wt. % neutral formaldehyde. lung tissue is soaked in 10 wt. % neutral formaldehyde for external fixation. After 24 hours, paraffin embedding and pathological section is performed. After the pathological section, Masson staining is used to observe the proliferation of fibers, as illustrated in FIG. 8.

1) Steps of Masson Trichromatic Method are as Follows.

1. The paraffin sections are deparaffinized to water.

2. The paraffin sections are chromized or precipitated with mercury removal salts (this step may be omitted for formaldehyde-fixed tissues).

3. The paraffin sections are washed with tap water and distilled water in sequence.

4. The nuclei is stained with Regaud hematoxylin or Weigart hematoxylin for 5 minutes to 10 minutes.

5. The paraffin sections are washed with water, and differentiated with hydrochloric acid and ethanol.

6. The paraffin sections are washed with distilled water.

7. The paraffin sections are stained with acid red-recovering solution of Masson ponceau for 5 minutes to 10 minutes.

8. The paraffin sections are rinsed with 2 wt. % aqueous glacial acetic acid for a while.

9. The paraffin sections are differentiated with 1 wt. % aqueous phosphomolybdic acid solution for 3 minutes to 5 minutes.

10. The paraffin sections are directly stained with aniline blue or light green liquor for 5 minutes.

11. The paraffin sections are rinsed with 0.2 wt. % aqueous glacial acetic acid for a while.

12. The paraffin sections are sealed with 95 wt. % alcohol, absolute alcohol, xylene clear, and neutral gum.

2) Fibrosis Score

When the score is 0 point, no fibroblasts cell exists

When the score is 1 point, the relative percentage of the number of fibroblasts to the number of epithelial cells is <25%.

When the score is 2 points, the relative percentage of the number of the fibroblasts to the number of the epithelial cells is 25% to 50%.

When the score is 3 points, the relative percentage of the number of the fibroblasts to the number of the epithelial cells is 50% to 75%.

When the score is 4 points, the relative percentage of the number of fibroblasts to the number of epithelial cells is >75%.

(4) Determination of Cytokine Levels in BALF

Figure 9:
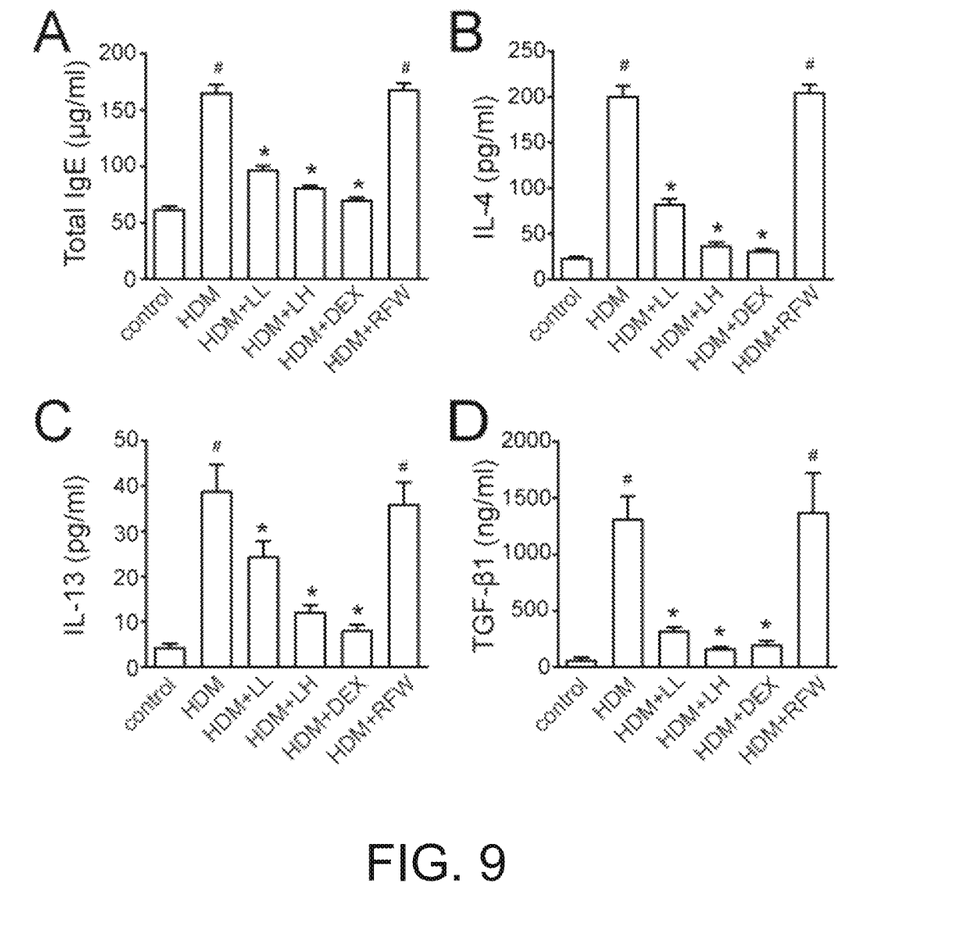
FIG. 9 illustrates the inflammatory factor change in BALF after the construction of the house dust mite-sensitized asthma mouse model. A is the effect of LZ_31 on the total IgE in BALF; B is the effect of LZ_31 on IL-4 in BALF; C is the effect of LZ_31 on IL-13 in BALF; D is the influence of LZ_31 on TGF-β1 in BALF. In #P<0.05, there is a statistical significance to compare difference with the control group; in *p<0.05, there is a statistical significance to compare difference with the HDM group.

The results are illustrated in FIG. 9, which is obtained by performing the procedures of the mouse total IgE ELISA testing kit, IL-4, IL-13, and TGF-β1 ELISA testing kit, respectively.

1) Mouse Total IgE Testing

1. Required reagents, standard product diluent and control are prepared and balanced to the room temperature.

2. Each well is added with 40 μL of diluent.

3. The corresponding wells are added with 10 μL of standard substance, control and sample to be detected, and multiple wells are set.

4. Each well is patted for 1 minute and attached with a sealing film, and incubated for 30 minutes at 37° C.

5. The solution is discarded, the plate is washed for 5 times, and patted to dry.

6. Each well except blank wells is added with 50 μL of IgE enzyme labeling reagent, mixed, and then attached with a sealing film, and incubated for 30 minutes at 37° C.

7. Step 5 of washing the plate is repeated.

8. Each well is added with the substrate color development liquid (100 μL each well), vibrated lightly and mixed uniformly, and developed for 15 minutes in a dark place at 37° C.

9. Each well is added with 50 μL of reaction stop solution.

10. Within 15 minutes after the end of the reaction, the plate is read in ELISA format (450 nm) using a microplate reader. An IgE ELISA standard curve is made and the concentration of IgE in each sample is calculated.

2) Mouse IL-4 Testing

1. Required reagents, standard product diluent and control are prepared and balanced to the room temperature.

2. Each well is added with 50 μL of diluent.

3. The corresponding wells are added with 50 μL of standard substance, control and sample to be detected, and multiple wells are set.

4. Each well is patted for 1 minute and attached with a sealing film, and incubated for 2 hours at the room temperature.

5. The solution is discarded, the plate is washed for 4 times and patted to dry.

6. Each well is added with 100 μL of IL-4 enzyme labeling reagent, mixed, and then attached with a sealing film, and incubated for 2 hours at the room temperature.

7. Step 5 of washing the plate is repeated.

8. Each well is added with the substrate developing solution (100 μL each well), kept out of the light, and incubated for 30 minutes at the room temperature.

9. Each well is added with 100 μL of reaction stop solution, and lightly vibrated and uniformly mixed.

10. Within 30 minutes after the end of the reaction, the plate is read in ELISA format (450 nm) using a microplate reader. An IL-4 ELISA standard curve is prepared and the IL-4 concentration in each sample is calculated.

3) Mouse IL-13 Testing

1. Required reagents, standard product diluent and control are prepared and balanced to the room temperature.

2. Each well is added with 50 μL of diluent.

3. The corresponding wells are added with 50 μL of standard substance, control and sample to be detected, and multiple wells are set.

4. Each well is patted for 1 minute, attached with a sealing film, and incubated for 2 hours at the room temperature.

5. The solution is discarded, the plate is washed for 5 times and patted to dry.

6. Each well is added with 100 μL of IL-13 enzyme labeling reagent, mixed, and then attached with a sealing film, and incubated for 2 hours at the room temperature.

7. Step 5 of washing the plate is repeated.

8. Each well is added with the substrate developing solution (100 μL each well), kept out of the light, and incubated for 30 minutes at the room temperature.

9. Each well is added with 100 μL of reaction stop solution, and lightly vibrated and uniformly mixed.

10. Within 30 minutes after the end of the reaction, the plate is read in ELISA format (450 nm) using a microplate reader. An IL-13 ELISA standard curve is prepared, and the IL-13 concentration in each sample is calculated.

4) Mouse TGF-β1 Testing

1. Required reagents, standard product diluent and control are prepared and balanced to the room temperature.

2. Sample activation

The sample is placed in an EP tube made of polypropylene material, and 20 μL of HCl is added to every 100 μL of sample.

After mixing uniformly, the sample is incubated for 10 minutes at the room temperature.

Acid in the sample is neutralized by adding 20 μL of 1.2N NaOH/HEPES to each tube.

After mixing uniformly, the sample is immediately used for the experiment (diluted by 1.4 times).

3. Each well is added with 50 μL of diluent.

4. The corresponding wells are added with 50 μL of standard substance, control and activated sample, and multiple wells are set.

5. Each well is patted for 1 minute, attached with a sealing film, and incubated for 2 hours at the room temperature.

6. The solution is discarded, the plate is washed for 4 times, and patted to dry.

7. Each well is added with 100 μL of TGF-β1 enzyme labeling reagent, mixed, then attached with a sealing film, and incubated for 2 hours at the room temperature.

8. Step 6 of washing the plate is repeated.

9. Each well is added with the substrate developing solution (100 μL each well), kept out of the light, and incubated for 30 minutes at the room temperature.

10. Each well is added with 100 μL of reaction stop solution, and lightly vibrated and uniformly mixed.

11. Within 30 minutes after the end of the reaction, the plate is read in ELISA format (450 nm) using a microplate reader. TGF-β1 ELISA standard curves are prepared, and the concentration of TGF-β1 in each sample is calculated.

Conclusions are as follows. At a cellular level, the *Ganoderma* tRFs has an inhibition effect on the excessive proliferation of the ASMC, and the inhibition effects of the *Ganoderma* tRFs 11, 25 and 31 are relatively obvious. In addition, the *Ganoderma* tRFs has different inhibition effects on the excessive secretion of ICAM-1 and VCAM-1 induced by TGF-β1, and in sum, the above effects of the *Ganoderma* tRFs_31 is the most obvious, and the fibronectin and IV type collagen levels induced by the TGF-β1 can be further inhibited; at the animal level, *Ganoderma* tRF_31 has significant inhibition effects on asthma airway hyperresponsiveness, airway fibrosis, inflammatory cell recruitment, Th-2 class inflammatory factors, and TGF-β1. Therefore, the application of the *Ganoderma* tRFs in the research and development of asthma drugs has a good application prospect.

What is claimed is:

1. A *Ganoderma* fungal RNA molecule, which is used in preparation of asthma prevention or treatment drugs,
wherein the *Ganoderma* fungal RNA molecule originates from transfer RNA molecule fragments (tRNA fragment, tRFs) of *Ganoderma* traditional Chinese medicine,
wherein a sequence of the tRFs of *Ganoderma* traditional Chinese medicine comprises a sequence selected from SEQ ID NO. 4 to NO. 6.

2. The *Ganoderma* fungal RNA molecule according to claim 1, wherein the tRFs of *Ganoderma* traditional Chinese medicine are double stranded RNA molecules, the tRFs of *Ganoderma* traditional Chinese medicine comprise an antisense sequence selected from SEQ ID NO. 4 to NO. 6 and a complementary sense sequence selected from SEQ ID NO. 10 to NO. 12.

3. The *Ganoderma* fungal RNA molecule according to claim 2, wherein the double stranded RNA molecules further comprise a 3' suspension.

4. The *Ganoderma* fungal RNA molecule according to claim 3, wherein a nucleotide sequence of an antisense and/or sense strand of the double stranded RNA molecules comprises at least one chemically modified nucleotide; wherein the chemical modification is selected from at least one of 1-methyl, 2-methyl, 5-methyl, 7-methyl, N2-methyl, N6-methyl, N2,N2-dimethyl, 2'-O-methyl, N6-isopentenyl, 2-methylthio-N6-isopentenyl, N6-threonic carbamoyl, N6-methyl-N6-threonic carbamoyl, 2-thio, 4-thio, N4-acetyl, 5-formyl, 3-(3-amino-3-carboxypropyl), 5-methoxy, 5-oxyacetic acid, 5-oxyacetic acid methyl ester, 5-methoxycarbonylmethyl, 5-methoxycarbonylmethyl-2'-O-methyl, 5-methoxycarbonylmethyl-2-thio, 5-aminoethyl-2-thio, 5-methylaminomethyl, 5-methylaminomethyl-2-thio, 5-aminoformylmethyl, 5-aminoformylmethyl-2'-O-methyl, 5-carboxymethylaminomethyl, 5-carboxymethylaminomethyl-2'-O-methyl, 5-carboxymethylaminomethyl-2-methyl, 5-taurine methyl, and 5-taurinemethyl-2-thio.

5. A drug for preventing or treating asthma, wherein an active ingredient comprises at least one of the transfer RNA molecule fragments of *Ganoderma* traditional Chinese medicine according to claim 1, and an optionally a pharmaceutically acceptable carrier, a diluent and/or an excipient.

6. The drug according to claim 5, wherein the drug further comprises a nucleic acid stabilizer.

7. A delivery carrier for preventing and treating asthma, comprising the double stranded RNA molecules according to claim 3, and an optionally a pharmaceutically acceptable carrier, a diluent and/or an excipient.

* * * * *

```
                             SEQUENCE LISTING

Sequence total quantity: 12
SEQ ID NO: 1            moltype = RNA   length = 19
FEATURE                 Location/Qualifiers
source                  1..19
                        mol_type = other RNA
                        organism = synthetic construct
SEQUENCE: 1
ggggatatct gataattgg                                                 19

SEQ ID NO: 2            moltype = RNA   length = 22
FEATURE                 Location/Qualifiers
source                  1..22
                        mol_type = other RNA
                        organism = synthetic construct
SEQUENCE: 2
gggcccttag cttaataggt ag                                             22

SEQ ID NO: 3            moltype = RNA   length = 19
FEATURE                 Location/Qualifiers
source                  1..19
                        mol_type = other RNA
                        organism = synthetic construct
SEQUENCE: 3
gggcccttag cttaatagg                                                 19

SEQ ID NO: 4            moltype = RNA   length = 22
FEATURE                 Location/Qualifiers
source                  1..22
                        mol_type = other RNA
                        organism = synthetic construct
SEQUENCE: 4
tgagttgtag tttaatttgg ga                                             22

SEQ ID NO: 5            moltype = RNA   length = 22
FEATURE                 Location/Qualifiers
source                  1..22
                        mol_type = other RNA
                        organism = synthetic construct
SEQUENCE: 5
gccaaaatag tttaaatggt ta                                             22

SEQ ID NO: 6            moltype = RNA   length = 22
FEATURE                 Location/Qualifiers
source                  1..22
                        mol_type = other RNA
                        organism = synthetic construct
SEQUENCE: 6
tcgagtctat ctatctccac ca                                             22

SEQ ID NO: 7            moltype = RNA   length = 19
FEATURE                 Location/Qualifiers
source                  1..19
                        mol_type = other RNA
                        organism = synthetic construct
SEQUENCE: 7
ccaattatca gatatcccc                                                 19

SEQ ID NO: 8            moltype = RNA   length = 22
FEATURE                 Location/Qualifiers
source                  1..22
                        mol_type = other RNA
                        organism = synthetic construct
SEQUENCE: 8
ctacctatta agctaagggc cc                                             22

SEQ ID NO: 9            moltype = RNA   length = 19
```

```
FEATURE             Location/Qualifiers
source              1..19
                    mol_type = other RNA
                    organism = synthetic construct
SEQUENCE: 9
cctattaagc taagggccc                                                        19

SEQ ID NO: 10       moltype = RNA  length = 22
FEATURE             Location/Qualifiers
source              1..22
                    mol_type = other RNA
                    organism = synthetic construct
SEQUENCE: 10
tcccaaatta aactacaact ca                                                    22

SEQ ID NO: 11       moltype = RNA  length = 22
FEATURE             Location/Qualifiers
source              1..22
                    mol_type = other RNA
                    organism = synthetic construct
SEQUENCE: 11
taaccattta aactattttg gc                                                    22

SEQ ID NO: 12       moltype = RNA  length = 22
FEATURE             Location/Qualifiers
source              1..22
                    mol_type = other RNA
                    organism = synthetic construct
SEQUENCE: 12
tggtggagat agatagactc ga                                                    22
```